United States Patent [19]

Krumkalns

[11] 4,282,030
[45] Aug. 4, 1981

[54] METHOD FOR PLANT GROWTH REGULATION

[75] Inventor: Eriks V. Krumkalns, Indianapolis, Ind.

[73] Assignee: Eli Lilly and Company, Indianapolis, Ind.

[21] Appl. No.: 193,857

[22] Filed: Oct. 3, 1980

[51] Int. Cl.³ .................. A01N 43/28; A01N 43/32
[52] U.S. Cl. ........................................... 71/90; 71/76
[58] Field of Search ...................... 71/90, 76

[56] References Cited

U.S. PATENT DOCUMENTS

| | | | |
|---|---|---|---|
| 4,090,861 | 5/1978 | Pilgram | 71/90 |
| 4,101,307 | 7/1978 | Clapot et al. | 71/90 |
| 4,127,402 | 11/1978 | Graham et al. | 71/90 |

FOREIGN PATENT DOCUMENTS 2549768 11/1968 Japan .
1345159 1/1974 United Kingdom .

OTHER PUBLICATIONS

Pilgram et al., J. Heterocyclic Chem., vol. 14, (1977), pp. 1035-1037.

Satsumabayashi et al., Bul. Chem. Soc. Japan, vol. 45, (1972), pp. 913-915.

Primary Examiner—Catherine L. Mills
Attorney, Agent, or Firm—Charles W. Ashbrook; Arthur R. Whale

[57] ABSTRACT

Compounds of the formula

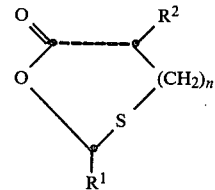

wherein
$R^1$ is trichloromethyl or trifluoromethyl
$R^2$ is hydrogen or methyl; and n is 0 or 1, are useful in regulating the growth of plants when applied to the plants, to the locus where plants are growing, or to plant seeds.

11 Claims, No Drawings

METHOD FOR PLANT GROWTH REGULATION

BACKGROUND OF THE INVENTION

This invention relates to a method for the regulation of plant growth employing certain substituted oxathiolanone-type compounds.

Several 1,3-oxathiolan-5-ones are known in the art. Pilgram, in U.S. Pat. No. 4,019,892, describes certain phenoxymethyl substituted 1,3-oxathiolan-5-ones which are alleged to be useful as herbicidal agents. Satsumabayaski et al., in *Bull. Chem. Soc. Japan*, 45, 913-915 (1972), describe the synthesis of a number of 2-alkyl and 2-phenyl-1,3-oxathiolan-5-ones. Also described is the preparation of 2-trichloromethyl-1,3-oxathion-6-one, a six membered heterocyclic ring compound. Additionally, several 2-haloalkyl-1,3-oxathiolan-5-ones are reported to have herbicidal activity by Okada in Japanese Pat. No. 25497/68.

That certain oxathiolanone-type compounds can be utilized to regulate the growth of various plant species is heretofore unknown. An object of this invention therefore is to provide a method of plant growth regulation employing certain 1,3-oxathiolan-5-ones and related compounds.

SUMMARY OF THE INVENTION

This invention provides a method for regulating plant growth comprising applying to a plant, to plant seeds, or to the locus of a plant an effective amount of an oxathiolanone-type compound of the formula

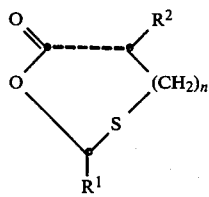

wherein:
$R^1$ is trichloromethyl, or trifluoromethyl
$R^2$ is hydrogen or methyl; and n is 0 or 1.

A preferred aspect of the invention comprises effecting plant growth regulation in barley employing a 1,3-oxathiolan-5-one of the above formula in which n is 0, $R^1$ is trichloromethyl or trifluoromethyl, and $R^2$ is hydrogen.

DETAILED DESCRIPTION OF THE INVENTION

The compounds required in the method of this invention are in general known in the art. The compounds can be prepared by condensation of a suitably substituted aldehyde with a thiolacetic acid derivative or a thiolactic acid derivative. Such condensation is illustrated by the following general reaction scheme:

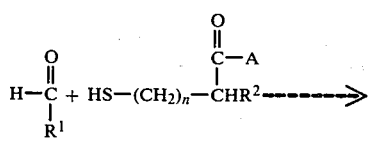

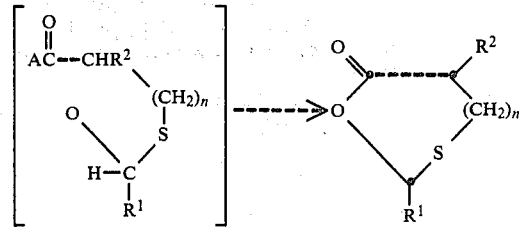

where n, $R^1$ and $R^2$ are as defined above, and A is a leaving group, for instance hydroxy, methoxy or ethoxy.

The condensation generally is accomplished by combining approximately equimolar quantities of the substituted aldehyde and the thiolacetic acid derivative or the thiolactic acid derivative in a mutual organic solvent such as benzene, toluene, xylene or the like. An excessive amount of either reactant can be utilized if desired. The reaction normally is catalyzed by the presence of an acid such as sulfuric acid or paratoluenesulfonic acid. When the reaction is carried out at a temperature of about 20° to about 150° C., it normally is substantially complete after about four to about thirty-six hours. Longer reaction times can be employed if desired.

The product of the condensation reaction can be isolated by neutralizing the reaction mixture, for example by washing the mixture with an aqueous base such as dilute sodium hydroxide or sodium bicarbonate, and then removing the reaction solvent by evaporation. The compound can be further purified if desired by routine methods including distillation, chromatography, and related techniques.

The preparation of representative compounds to be employed in the method of plant growth regulation as provided by this invention is presented below.

EXAMPLE 1

2-Trichloromethyl-1,3-oxathiolan-5-one

A solution of 29.4 g. of trichloroacetaldehyde and 24.0 g. of ethyl thiolacetate in 250 ml. of benzene containing 1 ml. of sulfuric acid was heated at reflux for six hours. The reaction mixture was cooled to room temperature and stirred for an additional twelve hours. The reaction mixture next was washed with water, dried, and the solvent was removed by evaporation under reduced pressure to provide 47.0 g. of crude product. The product was dissolved in 200 ml. of diethyl ether and washed with 100 ml. of 5% sodium bicarbonate. The organic layer was separated, dried, and the solvent was removed by evaporation under reduced pressure to afford an oil. The oil was distilled to provide 22.0 g. of 2-trichloromethyl-1,3-oxathiolan-5-one. B.P. 130°-140° C.

Analysis calculated for $C_4H_3Cl_3O_2S$; Theory: C, 21.67; H, 1.35; Cl, 48.08. Found: C, 21.96; H, 1.20; Cl, 48.10.

EXAMPLE 2

2-Trichloromethyl-4-methyl-1,3-oxathiolan-5-one

A solution of 44.1 g. of trichloroacetaldehyde and 42.4 g. of thiolactic acid in 400 ml. of benzene containing 1 ml. of concentrated sulfuric acid was heated at reflux for four hours. A dean-Stark trap was utilized for convenient removal of water from the reaction mixture.

The reaction mixture was cooled, filtered and concentrated to dryness by evaporation of the reaction solvent. The crude product thus formed was distilled to give 40 g. of 2-trichloromethyl-4-methyl-1,3-oxathiolan-5-one. M.P. 46°–47° C.

Analysis calculated for $C_5H_5Cl_3O_2S$; Theory: C, 25.50; H, 2.14. Found: C, 25.30; H, 2.01.

EXAMPLE 3

2-Trifluoromethyl-1,3-oxathiolan-5-one

A solution of 500 ml. of benzene containing 30 g. of trifluoroacetaldehyde, 30 g. of ethyl thiolacetate and 10 ml. of concentrated sulfuric acid was stirred at room temperature for sixteen hours. The mixture was heated at reflux for eight hours, and then was cooled to room temperature and stirred for an additional twelve hours. The reaction solvent next was removed by evaporation, and the residue was dissolved in diethyl ether and neutralized to pH 7 with aqueous sodium bicarbonate. The organic layer was separated, washed with water, dried, and the solvent was removed by evaporation under reduced temperature to provide an oil. The oil solidified upon standing, and was recrystallized from ethanol to give 9.0 g. of 2-trifluoromethyl-1,3-oxathiolan-5-one. M.P. 62°–63° C.

Analysis calculated for $C_4H_3F_3O_2S$; Theory: C, 27.91; H, 1.76. Found: C, 26.17; H, 1.58.

EXAMPLE 4

2-Trichloromethyl-1,3-oxathian-6-one

A solution of 3.8 g. of 3-(1-hydroxy-2,2,2-trichloroethyl)thiopropionic acid in 15 ml. of acetic anhydride was heated at reflux for four hours. The reaction mixture was then cooled to room temperature and the reaction solvent was removed by evaporation under reduced pressure. The crude product thus formed was purified by chromatography over silica gel, eluting with fifty percent ethyl acetate in hexane. The appropriate fractions were combined and the solvent was removed by evaporation to give 4.2 g. of product. Crystallization of the product from hexane afforded 2-trichloromethyl-1,3-oxathian-6-one. M.P. 65°–67° C.

Analysis calculated for $C_5H_5Cl_3O_2S$; Theory: C, 25.50; H, 2.14; Cl, 45.16; S, 13.61. Found: C, 26.14; H, 2.46; Cl, 42.43; S, 13.73.

The compounds defined by the above formula are employed in the regulation of growth of various plant species according to the method of this invention. Typical plant responses which are embraced by terms such as "plant growth regulation" include inhibition of vegetative growth in herbaceous plants, control of flowering, inhibition of seed formation, control of fruiting, delay in maturation, and related growth regulatory responses.

The growth regulatory action of the compounds defined above may be advantageously employed in various ways. The production of shorter and thicker stems in cereal grains such as wheat, barley and oats may reduce the tendency toward lodging and thus result in reduced economic loss due to adverse weather conditions. The control of flowering and fruiting may be advantageous in the production of seedless fruit and for hybridization. Modifying the vegetative process or altering the time of flowering and fruiting may result in more advantageous harvest dates or increased or modified flower, fruit or seed production. Useful chemical pruning of trees, shrubs, ornamentals and nursery stock may be obtained. Retardation of senescence of perishable fruits and vegetables can be effected to prolong storage life. Other applications employing compounds defined herein will suggest themselves to those skilled in the art of agriculture and plant growth regulation.

The various plant species whose growth can be regulated according to the method of this invention includes bean species such as soybean, the various green snapbean varieties, as well as crop species such as corn, wheat, rye, flax, rice and barley. A preferred method according to this invention comprises a compound herein defined to a cereal grain crop, particularly barley.

The method for regulating the growth of plants provided by this invention comprises applying to the plants an effective amount of a plant growth regulator as defined by the above general formula. The application of active compound can be accomplished by contacting the foilage of the plants with the active compound, or if desired simply applying the compound to the habitat in which the plant whose growth is to be regulated is growing. The compounds can be applied directly to seeds if desired.

The specific amount of active plant growth regulator compound to be applied according to the new method will of course be determined by one or more of several factors, including the particular plant species being treated, the mode of application, the soil texture and moisture content, the particular time during the growing cycle the method is practiced, and related factors. Generally, the oxathiolanone-type plant growth regulators will be applied at an effective rate of about 0.1 to about 15 pounds per acre, more preferably at an effective rate of about 1 to about 5 pounds per acre. When employed as seed treatment agents, the compounds will usually be applied at a rate of about 0.5 to about 15 ounces per 100 pounds of seeds, and preferably at a rate of about 1 to about 4 ounces per 100 pounds of seed.

For use as contemplated according to the method of this invention, the oxathiolanone-type growth regulator compounds are formulated into compositions suited to soil surface or foliar application to plants and areas where plants are growing and for use as seed treatments. Such compositions are, in general, similar to the herbicidal compositions containing oxathiolanones as described in U.S. Pat. No. 4,019,892. For example, the compounds can be formulated with any number of well known and routinely used agronomically-acceptable carriers, diluents, excipients and the like. The compositions may take the form of wettable powders, dusts, granules, solutions, emulsifiable concentrates, emulsions, suspension concentrates and the like. Such compositions generally contain from about 1 to about 95 percent active ingredient.

A preferred composition for use according to the present method is a wettable powder. Wettable powders generally contain from about 20 to about 80 percent by weight of active ingredient. The remainder of the composition consists of solid carriers and wetting agents. Commonly utilized solid carriers include bentonite, fuller's earth, diatomaceous earth, diatomaceous silica, talc, chalk, hydrated silica, expanded mica, and related carriers. Wetting agents and surfactants commonly employed include condensed aryl sulfonic acids, sodium lignosulfate, sulfonateoxide condensate blends, alkyl aryl polyether alcohols, anionic and nonionic wetting agents, and the like.

Another commonly used composition form is a dust. Dusts generally contain about 5 to about 10 percent by weight of active ingredient admixed with a solid carrier such as clay or fuller's earth or the like.

Granules represent another important form of composition to be employed in the present method. Granules generally contain about 1 to about 30 percent by weight of active ingredient, admixed with a solid carrier such as silica or clay. Slow release modifiers such as polymers can be employed if desired. Also, binding agents such as sugar derivatives and polyvinylpyrrolidones can be incorporated into such compositions.

The compounds employed in the method of this invention can be used individually or in a mixture with one or more other active compounds. For example, the oxathiolanone-type compounds defined herein can be used in combination with other plant growth regulators such as the polymeric N-vinyl-2-oxazolidinones, N-dimethylamino-1,2,3,6-tetrahydrophthalamic acid and its salts, pyridones, mefluidide and its related compounds as described in U.S. Pat. No. 3,894,078, the pyrimidinemethanols described in U.S. Pat. No. 4,002,628, and other commonly used plant growth regulators. The oxathiolanone-type compounds can also be employed in combination with other commonly used agricultural chemicals such as herbicides, fungicides, insecticides and plant bactericides.

The plant growth regulator activity of the compounds defined above has been demonstrated for several representative compounds in standard greenhouse studies. In a typical greenhouse plant growth regulator screen, the compounds were evaluated on several plant species including soybean and barley. The compounds to be evaluated were formulated by dissolving 20 mg. of test compound in 30 ml. of a solution containing 3 ml. of a 1:1 v/v solution of ethanol and acetone and 27 ml. of deionized water containing 300 ppm Toximul R and 400 ppm Toximul S surfactants. (Toximul R and Toximul S are proprietary blends of anionic and nonionic surface active agents commonly employed in pesticide formulations. They are manufactured by Stepan Chemical Co., Northfield, Ill.). The formulated compounds were evaluated as a soil drench and as a foliar spray. The formulation was diluted with water and applied to the soil in which the various plant species were growing. Foliar spray applications were made with a DeVilbiss atomizer.

Evaluations of plant growth regulator effects and plant injury were made on a scale of 0 to 3, with 0 being no effect and 3 being a distinct or severe effect. A "+" sign is used to designate growth promotion, while a "−" sign is employed to designate inhibition or depression. Various plant growth regulator effects were observed, including effect on height, effect on branching, and effect on flowering. The results of typical evaluations are presented in Tables I–III.

TABLE I

| Plant Growth Regulator Effect on Height | | | | |
|---|---|---|---|---|
| Compound of Example No. | Application Method | Application Rate lbs/A | Soybean | Barley |
| 1 | foliar | 3 | −1 | −1 |
|   | soil drench | 5 | 0 | −3 |
| 2 | foliar | 5 | +1 | 0 |
|   | soil drench | 5 | +1 | 0 |
| 3 | foliar | 5 | −1 | −2 |
|   | soil drench | 5 | 0 | 0 |

TABLE I-continued

| Plant Growth Regulator Effect on Height | | | | |
|---|---|---|---|---|
| Compound of Example No. | Application Method | Application Rate lbs/A | Soybean | Barley |
| 4 | foliar | 5 | 0 | 0 |
|   | soil drench | 5 | −3 | 0 |

TABLE II

| Plant Growth Regulator Effect on Branching | | | |
|---|---|---|---|
| Compound of Example No. | Application Mode | Application Rate lbs/A | Soybean |
| 1 | foliar | 5 | +1 |
|   | soil drench | 5 | +1 |
| 2 | foliar | 5 | +1 |
|   | soil drench | 5 | +2 |
| 3 | foliar | 5 | +1 |
|   | soil drench | 5 | 0 |
| 4 | foliar | 5 | 0 |
|   | soil drench | 5 | +2 |

TABLE III

| Plant Growth Regulator Effect on Flowering | | | |
|---|---|---|---|
| Compound of Example No. | Application Mode | Application Rate lbs/A | Barley |
| 1 | foliar | 5 | 0 |
|   | soil drench | 5 | −3 |
| 2 | foliar | 5 | +2 |
|   | soil drench | 5 | 0 |
| 3 | foliar | 5 | −2 |
|   | soil drench | 5 | −2 |
| 4 | foliar | 5 | −1 |
|   | soil drench | 5 | 0 |

I claim:

1. A method for regulating plant growth comprising applying to a plant an amount effective to provide plant growth regulation of a compound of the formula

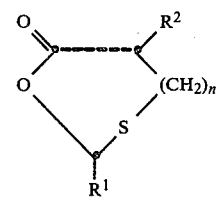

wherein:

$R^1$ is trichloromethyl, or trifluoromethyl;

$R^2$ is hydrogen or methyl; and n is 0 or 1.

2. The method of claim 1 employing a compound wherein n is one.

3. The method of claim 2 employing a compound wherein $R^2$ is hydrogen.

4. The method of claim 3 employing a compound wherein $R^1$ is trichloromethyl.

5. The method of claim 1 employing a compound wherein n is 0.

6. The method of claim 5 employing a compound wherein $R^2$ is hydrogen.

7. The method of claim 6 employing a compound wherein $R^1$ is trichloromethyl.

8. The method of claim 6 employing a compound wherein $R^1$ is trifluoromethyl.

9. The method of claim 5 employing a compound wherein $R^2$ is methyl.

10. The method of claim 9 employing a compound wherein $R^1$ is trichloromethyl.

11. The method according to claim 1 when applied to barley.

* * * * *